United States Patent [19]

Benardella

[11] Patent Number: Plant 6,783

[45] Date of Patent: May 9, 1989

[54] MINIATURE ROSE PLANT NAMED GEE GEE

[75] Inventor: Frank A. Benardella, Old Tappan, N.J.

[73] Assignee: John C. Walter, Grand Saline, Tex.

[21] Appl. No.: 145,457

[22] Filed: Jan. 5, 1988

[51] Int. Cl.[4] ..... A01H 5/00

[52] U.S. Cl. ..... Plt./8

[58] Field of Search ..... Plt./7-8

*Primary Examiner*—Robert E. Bagwill

[57] ABSTRACT

A new and distinct variety of miniature rose plant characterized by (1) distinctive yellow-orange blooms and buds borne singly, but prolifically, on (2) a vigorous, compact plant with abundant green foliage.

1 Drawing Sheet

The present invention relates to a new and distinct variety of rose plant of the miniature rose class, which was originated by my crossing as seed parent the miniature rose known as "Rise N Shine", (U.S. Plant Pat. No. 4,231) and the floribunda rose known in the United States as "Patricia," (Korpatri).

Among the novel characteristics possessed by this new variety which distinguish it from its parents and all other varieties of which I am aware are: (1) prolific blooms of yellow-orange, (2) blooms borne singly and very seldom clustered, (3) a soft fruity fragrance, (4) a well proportioned plant which is vigorous and shows off its blooms well against its green foliage, and (5) a plant which grows well both in the greenhouse and outdoors, is good for growing in pots, and provides excellent garden decoration as well as cut flowers.

The present variety of miniature rose was originated by me in Bergen County, N.J. Carefully controlled conditions and asexual reproduction by cuttings of the new variety as performed by me in Bergen County, N.J. show that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new rose variety, with color terminology in accordance with The Royal Horticultural Society Colour Chart (RHSCC) except where common dictionary terms of color definition are employed.

Type: Hardy, dwarf, bushy, upright, seedling, greenhouse, outdoors, cut flowers, garden decoration, potted plant.

Class: Miniature.

*International identification.*—Variety: Bengee.

*Commercial synonym.*—Gee Gee.

THE FLOWER

Observations were made from specimens grown outdoors at Bergen County, N.J., U.S.A. in September 1987.

Type: Miniature.

Blooming habit: Recurrent.

Bud:

*Size.*—Medium for miniature.

*Form.*—Pointed.

*Color.*—When sepals first divide: Yellow-orange (18-B). When petals begin to unfurl: Yellow-orange (18-B). When half-blown: Inside of petals: Yellow-orange (18-B). Outside of Petals: Yellow-orange (18-C).

*Sepals.*—Long "Toothed" sepals often rise above the bud (one often longer than the rest).

*Peduncle.*—Average length 1¼", erect, stable, green color.

Bloom:

*Size.*—1½" to 1¾" when fully expanded.

*Borne.*—Singly (prolifically).

*Form.*—High centered at first, becoming flat, petals remaining loosely rolled outward.

*Petalage.*—20 to 25 petals under normal conditions.

*Color.*—During first two days: Inner petals at center of flower: Yellow-orange (18-A). Outer petals: Yellow-orange (18-C). Base of petals (point of attachment): Yellow-orange (18-B). Reverse of petals: Yellow-orange (18-C). General tonality from a distance: Yellow-orange (18-B).

*Color change.*—As bloom ages: Yellow-orange (18-C) (becomes lighter). General tonality: Yellow-orange (18-C). After three or more days: Yellow-orange (19-D (becomes even lighter).

Petals:

*Texture.*—Fairly thick.

*Appearance.*—Satiny both inside and outside.

*Form.*—Wide with edges rolling to 3 points.

*Arrangement.*—Regularly arranged.

*Petaloids in center.*—Very few.

*Persistance.*—Petals drop off cleanly.

*Fragrance.*—Very slight fruity fragrance.

*Lasting quality.*—Buds open quickly to full blown outdoors in warm weather, blooms keep well in refrigerator, a good cut flower.

REPRODUCTIVE ORGANS

Stamens, filaments and anthers:

*Arrangement.*—Evenly arranged around styles.

*Color.*—Yellow.

Pollen color: Yellow.

Styles: Uneven length, thin, tightly bunched.

Stigmas: Greenish yellow color.

Hips:

*Shape.*—Pear.

*Size.*—$\frac{3}{8}''$ long, $\frac{1}{4}''$ diameter.

*Color.*—Green, when mature both hip and peduncle turn yellow and drop off usually.

*Seeds.*—Have not observed any.

PLANT

Form: Upright and compact.

Growth: Vigorous with uniform branching.

*Height attained.*—18" to 20".

Foliage: Mostly 7 leaflets.

*Size.*—Medium with delicate appearance.

*Quantity.*—Abundant.

*Color.*—New foliage: upper side: Light green. under side: Lighter green. Old foliage: upper side: Green. under side: Lighter green.

*Shape.*—Oval pointed.

*Texture.*—Upper side: matt, indented veins prominent. Under side: matt, raised veins.

*Edge.*—Quite serrated.

*Serration.*—Uniform indentations appearing reddish green.

*Leaf stem.*—Reddish green to green on both sides.

*Stipules.*—Medium length, pointed curved auricles.

*Disease resistance.*—Blackspot, good; Mildew, good; Rust, good.

Wood:

*New wood.*—Color: green, Bark: smooth.

*Old wood.*—Color: green, Bark: smooth.

Thorns:

*Quantity.*—Few spaced irregularly on main canes and laterals.

*Form.*—Needle shaped with slightly expanded base.

*Length.*—Medium — $\frac{1}{4}''$ long.

*Color.*—Beige when both young and mature.

*Position.*—Very irregular.

Prickles:

*Quantity.*—Very few on main canes or laterals.

Winter hardiness: Needs some protection at 10° or lower. Can use a mound of dirt or leaves.

I claim:

1. A new and distinct variety of rose plant of the miniature rose class, substantially as herein shown and described, characterized particularly by profuse yellow-orange blooms with firm, satiny petals, borne singly on an upright, bushy plant with abundant foliage, said plant being easy to propagate from cuttings, and said blooms being long-lasting both on the plant and as cut flowers.

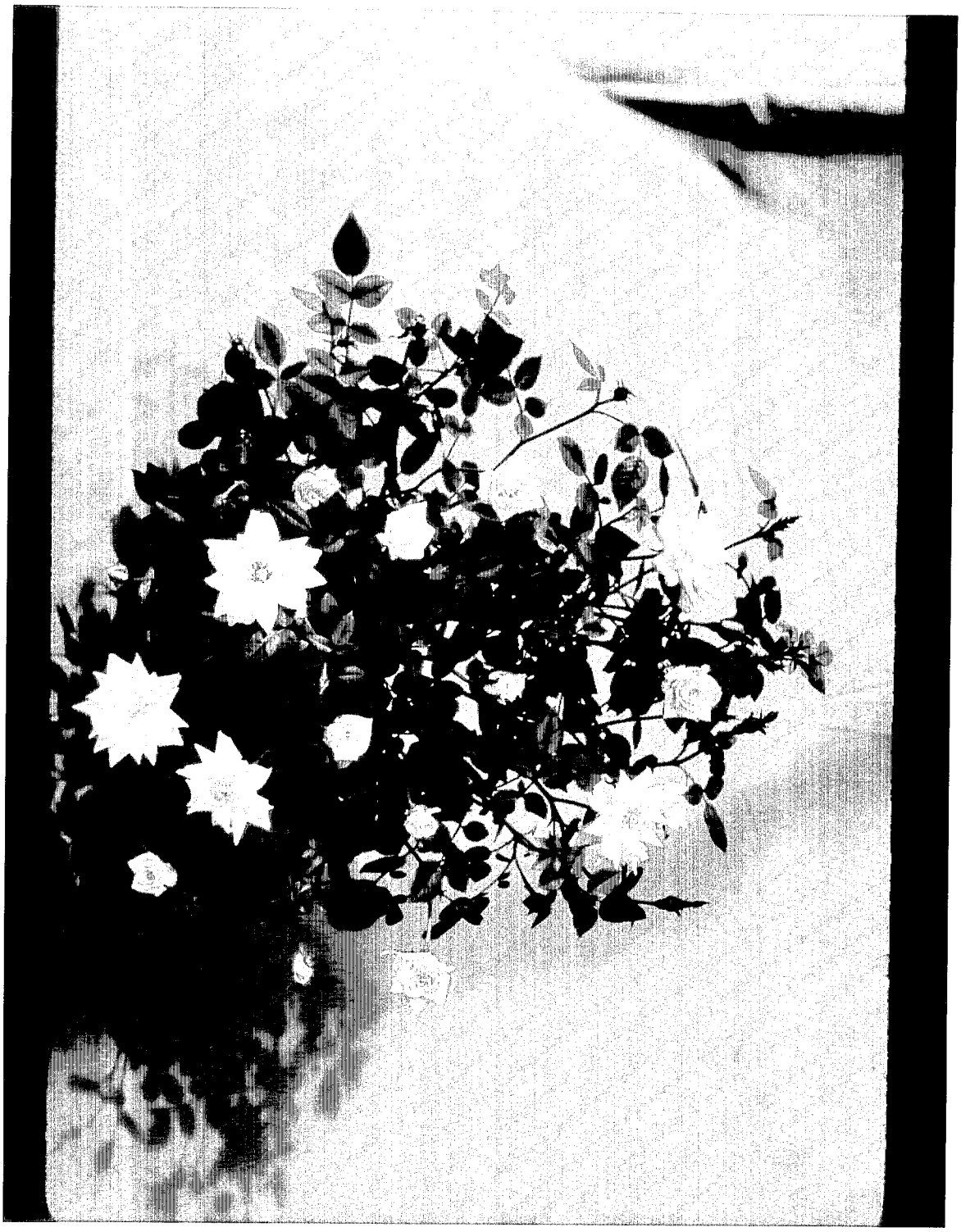

* * * * *